US007201735B2

(12) United States Patent
Atkin et al.

(10) Patent No.: US 7,201,735 B2
(45) Date of Patent: Apr. 10, 2007

(54) POWERED BREAST PUMP

(76) Inventors: Edward Atkin, 4 Redington Road, Hampstead, London NW3 (GB); Roger Leonard Williams, 5 Tudor Rise, Broxbourne, Hertfordshire EN10 7HB (GB); Mark John Wortley, 42 Waldingfield Road, Sudbury, Suffolk CO10 2PU (GB)

( * ) Notice: Subject to any disclaimer, the term of this patent is extended or adjusted under 35 U.S.C. 154(b) by 0 days.

(21) Appl. No.: 10/900,710

(22) Filed: Jul. 28, 2004

(65) Prior Publication Data
US 2005/0101908 A1 May 12, 2005

(30) Foreign Application Priority Data
Aug. 1, 2003 (GB) ................. 0318086.6

(51) Int. Cl.
*A61M 1/06* (2006.01)
(52) U.S. Cl. ..................................... 604/74
(58) Field of Classification Search ........... 604/74–76, 604/73, 346, 30–38, 65, 66, 67, 120, 121; 601/6
See application file for complete search history.

(56) References Cited

U.S. PATENT DOCUMENTS

| 5,007,899 | A | * | 4/1991 | Larsson ....................... 604/74 |
| 5,571,084 | A | * | 11/1996 | Palmer ........................ 604/74 |
| 5,601,531 | A | * | 2/1997 | Silver ........................... 604/74 |
| 5,676,525 | A | * | 10/1997 | Berner et al. ............... 417/44.1 |
| 5,810,772 | A | * | 9/1998 | Niederberger ............... 604/74 |
| 5,869,940 | A |   | 2/1999 | Parsadayan |
| 6,045,529 | A |   | 4/2000 | Nüesch |
| 6,257,847 | B1 | * | 7/2001 | Silver et al. ................. 417/415 |
| 6,383,163 | B1 | * | 5/2002 | Kelly et al. .................. 604/74 |
| 6,547,756 | B1 | * | 4/2003 | Greter et al. ................. 604/74 |
| 6,749,582 | B2 | * | 6/2004 | Britto et al. .................. 604/74 |
| 2003/0139702 | A1 |   | 7/2003 | Kampf et al. |

FOREIGN PATENT DOCUMENTS

| DE | 101 23 516 A | 1/2003 |
| JP | 2001-259023 | 9/2001 |
| WO | WO 00/57934 A | 10/2000 |
| WO | 01/47577 A | 7/2001 |
| WO | WO 01/47577 A | 7/2001 |

* cited by examiner

*Primary Examiner*—Manuel Mendez
(74) *Attorney, Agent, or Firm*—Eric Bram

(57) ABSTRACT

A powered breast pump has user input means which enable a user to control the pump in a "learn" mode. When the pump is switched to a "run" mode, it mimics the pumping cycle established by the user in the "learn" mode. The pump may be continuously operated in "learn" mode, in which case it functions as a power-assisted breast pump.

23 Claims, 9 Drawing Sheets

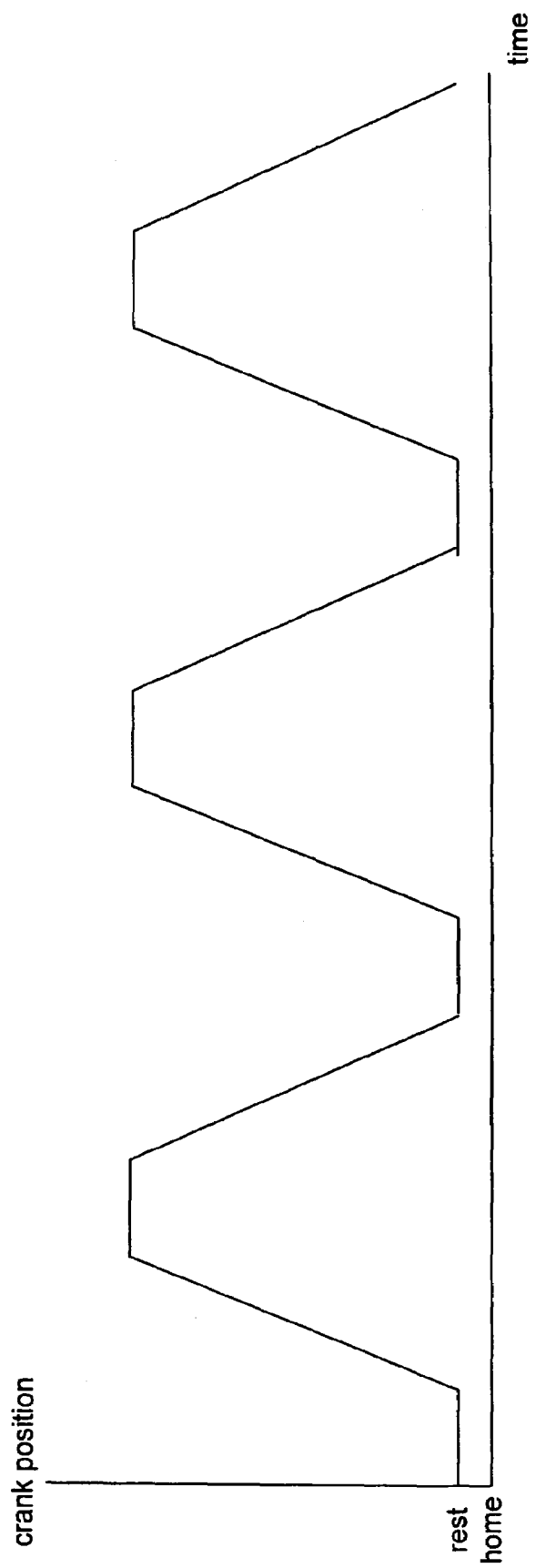

POWERED BREAST PUMP

FIELD OF THE INVENTION

The present invention relates to a powered breast pump system, comprising a motorised breast pump, user input means and a controller.

BACKGROUND TO THE INVENTION

WO-A-01/47577 discloses a programmable powered breast pump apparatus. The disclosed breast pump apparatus is programmed by recording control data on or in a data carrier which is then inserted into the breast pump apparatus. The control data is read from the data carrier and controls the pumping cycle.

The breast pump apparatus disclosed in WO-A-01/47577 suffers from the disadvantage that the programming process is complex.

U.S. Pat. No. 5,571,084 discloses a powered breast pump in which the user has some limited control over the pumping cycle. The limited control that the user has is itself a problem.

SUMMARY OF THE INVENTION

It is an object of the present invention to provide a powered breast pump system with improved user control.

It is another object of the present invention to provide a powered breast pump that can be trained.

A powered breast pump system, according to the present invention, is characterised in that the controller is configured to control the pumping operation of motorised breast pump such that the suction produced by the pump follows a suction level control signal, produced by operation of the user input means during pumping.

Thus, since the user has instantaneous control over the suction, the user can have fine control over the profile of the pumping cycle and vary the cycle with time so that the pumping can be optimised for effectiveness and/or comfort.

The controller may configured to operate the motorised breast pump in a learn mode, in which said suction level control signal is followed, and a run mode, in which the controller controls the pumping operation of the motorised breast pump so as to mimic previous learn mode operation.

The mimicry need not be exact and it has been found that it is satisfactory to obtain a few key parameters and control the pump using these. Therefore, preferably, the controller is configured to store parameters defining a pump operation cycle during learn mode operation. The parameters may comprise suction stroke velocity, relaxation stroke velocity, suction hold duration, rest hold duration, stroke length and suction stroke start position. Average values are preferably used for the velocity parameters.

Preferably, the motorised breast pump comprises a motorised pump unit, a handheld unit for receiving a user's breast and capturing expressed milk and tubing connecting the pump unit to the handheld unit and containing a working fluid which is pumped back and forth by the motorised pump unit for varying the pressure within a milk receiving chamber in the handheld unit.

Preferably, the motorised breast pump comprises a motorised pump unit, a handheld unit for receiving a user's breast and capturing expressed milk and tube connecting the pump unit to the handheld unit and containing a working fluid which is pumped back and forth by the motorised pump unit for varying the pressure within a milk receiving chamber in the handheld unit. More preferably, the handheld unit includes a flexible diaphragm separating the working fluid from the milk receiving chamber.

The motorised pump unit preferably comprises two pumps connected to respective handheld units by respective tubes and driven in phase by a shared motor. If the units were to be driven out of phase, the pumping cycle profile would need to be symmetrical to avoid different cycles being followed by each handheld unit. Driving the units in phase, means that asymmetrical profiles are possible.

Preferably, the or each handheld unit comprises a removable head which may include a diaphragm and a cap connected to the tube. The diaphragm and the cap may be separable. Advantageously, the removable head can be replaced by a similar manual head including operating means for manually varying the pressure in the milk receiving chamber.

Preferably, the user input means are configured such that the user operations for controlling the motor in the learn mode resemble the user operation of the operating means for manually pumping with a manual breast pump. More preferably, the operating means comprises a hand operable lever which can be operated with the hand that is holding the body. This form of user control has been found to be particularly advantageous in both the manual pumping, which can be physically demanding, and in learn mode where it gives easy and intuitive fine control to the user.

BRIEF DESCRIPTION OF THE DRAWINGS

FIG. 10 is a plot illustrating three "run" mode pumping cycles of the system of FIG. 1.

DETAILED DESCRIPTION OF AN EMBODIMENT

An embodiment of the present invention will now be described, by way of example only, with reference to the accompanying drawings.

Figure 1:
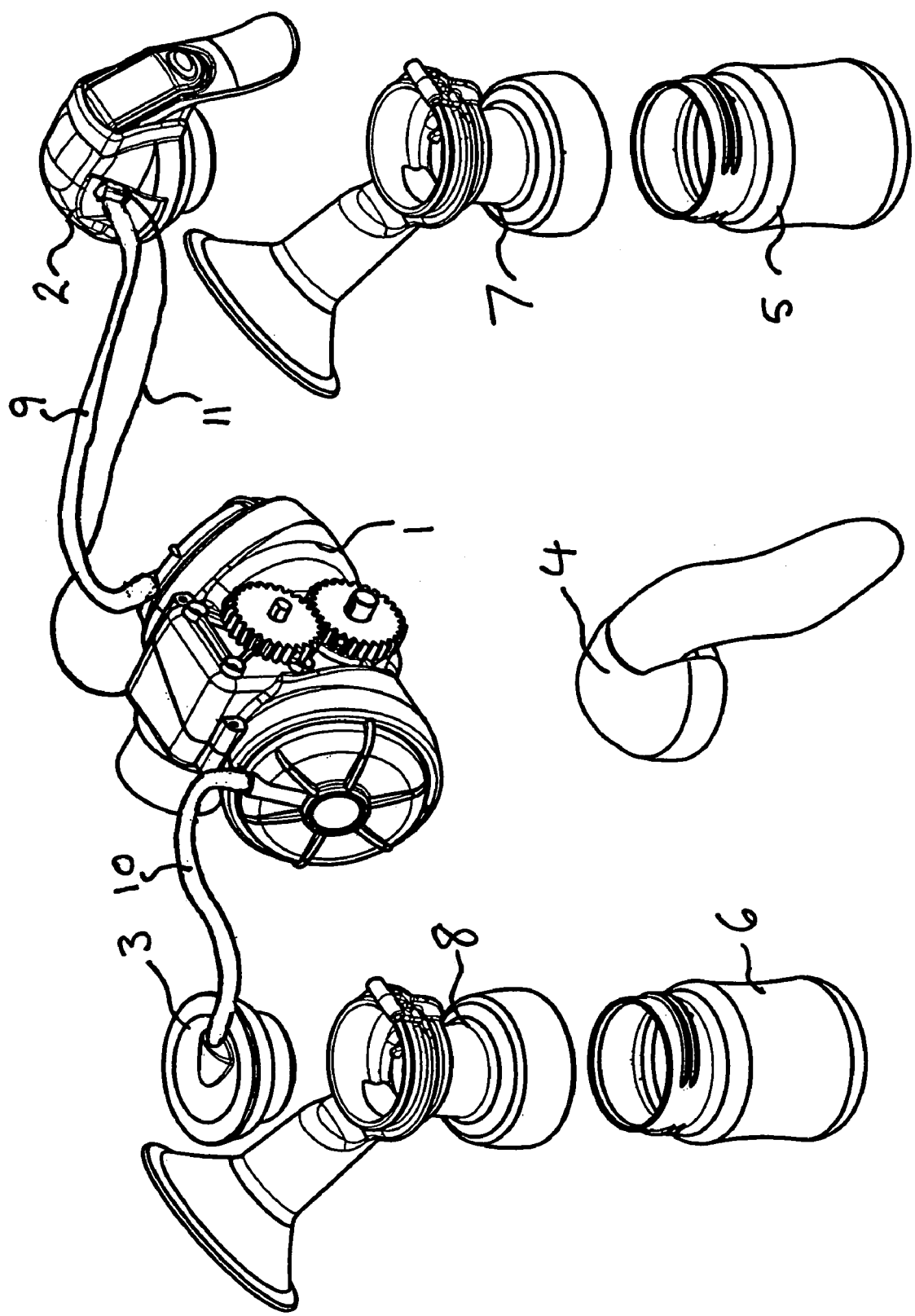
FIG. 1 shows a breast pump system according to the present invention.

Referring to FIG. 1, a breast pump system according to the present invention comprises a pneumatic pump 1 (shown without its casing), a master head 2, a slave head 3, a manual head 4, first and second feeding bottles 5, 6 and first and second identical bodies 7, 8. The master and slave heads 2, 3 are connected to the pump 1 by first and second flexible tubes 9, 10. The flexible tubes 9, 10 are 1.3 m long. A multi-core electrical lead 11 also extends from the master head 2 to the pump 1.

The bodies 7, 8 can be coupled to the necks of the bottles 5, 6 by screw fittings. The manual head 4, the bodies 7, 8 and the feeding bottles 5, 6 are very similar to the components of the Avent (RTM) ISIS (RTM) breast pump product. Further information regarding the operation of the manual head 4 in combination with a body 7, 8 and a feeding bottle 5, 6 can be obtained from EP-A-0733376.

Figure 2:
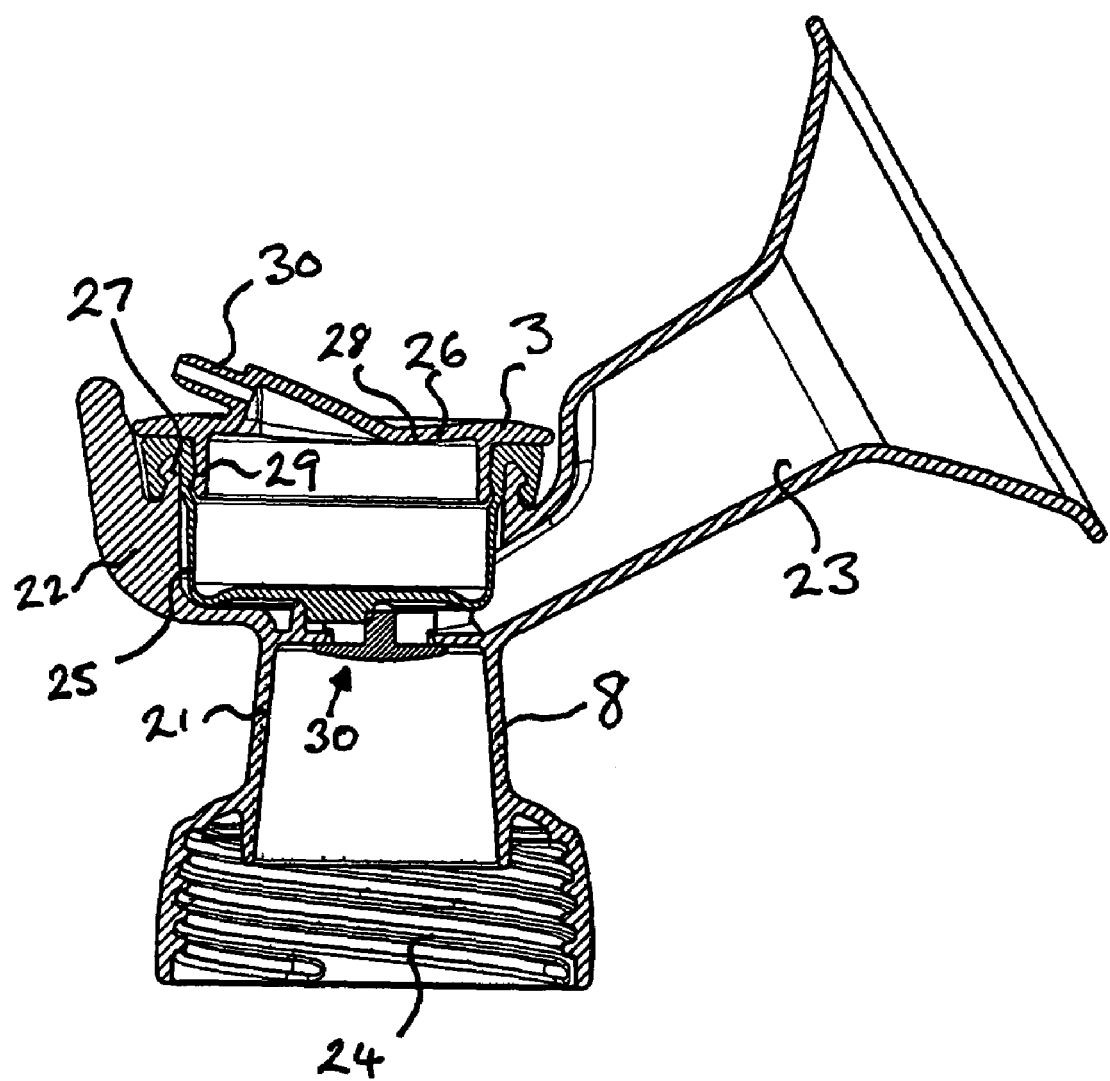
FIG. 2 is a sectional view of the slave head mounted to a body.

Referring to FIG. 2, the second body 8 comprises a neck 21, a cup 22 supported on the neck and a trumpet 23 projecting from the side of the cup 22. The bottom of the neck is flared and provided with an internal thread 24 for screwing the body 8 onto a bottle 5, 6. The trumpet 23 is inclined upwards and, in use, receives the nipple and surrounding breast portion of the user and is sealed thereby. A passageway extends from the open, distal end of the trumpet 23 through the bottom of cup 22 and the neck 21 to the open, bottom end of the neck 21. A valve 30 is provided between the cup 22 and the neck 21. The valve 30 is closed when the pressure in the cup 22 drops relative to the pressure in the neck 21 and opens when the pressure in the cup 22 rises to match the pressure in the neck 21.

The slave head 3 comprises a cup-shaped elastomeric diaphragm 25 and a cap 26. The diaphragm 25 is received within the cup 22. The rim of the diaphragm 25 is turned back on itself to form a channel 27 which receives the rim of the cup 22 to secure the diaphragm in the cup 22. The cap 26 comprises a disc 28, which is large enough to cover the interior of the diaphragm 25, and an annular flange 29 which projects coaxially from the disc 28. The flange 29 is received snugly in the mouth of the cup-shaped diaphragm 25 to form an air-tight seal between the cap 26 and the diaphragm 25. A nipple 30 projects from the exposed face of the disc 28. A channel extends through the nipple 30 and opens into the space within the diaphragm 25. In use, the nipple 30 is connected to the pump 1 by the second flexible tube 10 and, when the pump 1 sucks air through the second flexible tube 10, the floor of the cup-shaped diaphragm 25 is lifted, reducing the pressure within cup 22 and trumpet 23, closing the valve 30 and encouraging the expression of milk from the user's breast.

Figure 3:
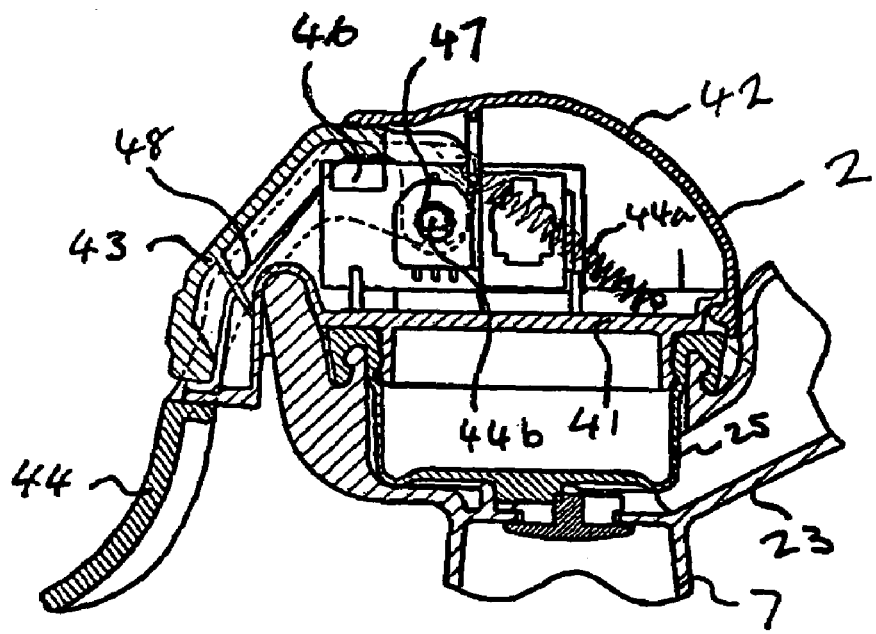
FIG. 3 is a sectional view of the master head and part of a body.

Referring to FIG. 3, the first body 7 is identical to the second body 8 described above. The master head 2 comprises a base 41, similar to the cap 26 of the slave head 3, and a domed body 42 affixed to the base 41.

Figure 4:
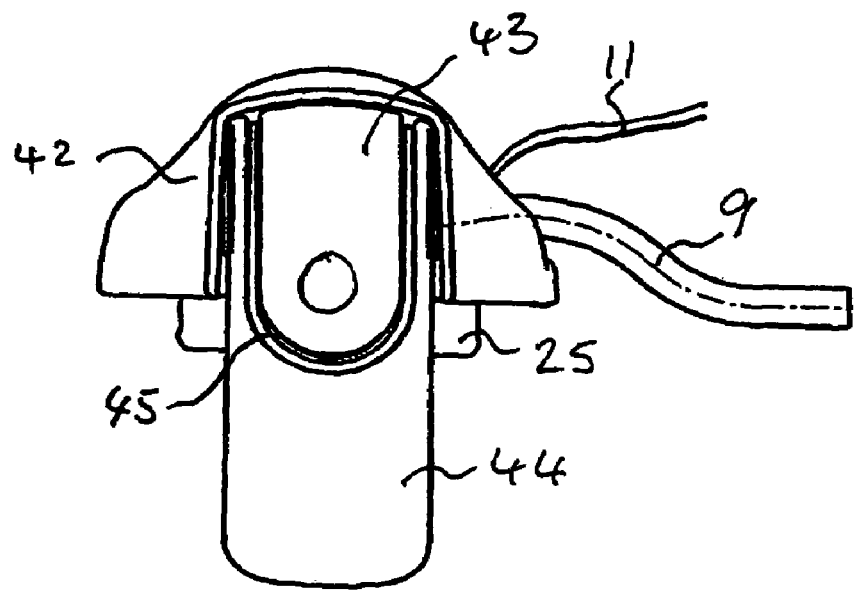
FIG. 4 is a rear view of the master head.

Referring also to FIG. 4, an arm 43 and a lever 44 extend from the back of the domed body 42. The overall form of the arm 43 and the lever 44 resembles the operating lever 12 of the manual head 4. The lever 44 has a longitudinal slot 45 in its proximal end and the arm 43 projects into the slot 45, substantially filling it. The proximal end of the lever 44 extends into the domed body 42 where it is attached to a fulcrum.

A push-to-make switch 46 is mounted in the domed body 42. The arm 43 projects generally horizontally into the domed body 42 over the switch 46 and has a boss which engages the switch's actuator. The arm 43 is pivoted at its proximal end so that pressing of the arm 43 towards the cup 22 closes the switch 46. A resilient finger 48 projects from the back of the arm 43 and bears against an extension 49 of the base 41 to bias the arm 43 away from the cup 22.

The lever 44 is biased outwards by a spring 44a within the domed body 42. The lever 44 is pivoted at its proximal end on the same axis as the arm 43. The pivot arrangement of the lever 44 includes a stub 44b that passes through a preset-type potentiometer 47 so that the wiper of the potentiometer 47 moves when the lever 44 is pivoted.

A nipple (not show) projects from the base 41 into a recess in the side of the domed body 42 and is connected to second tube 11.

Figure 5:
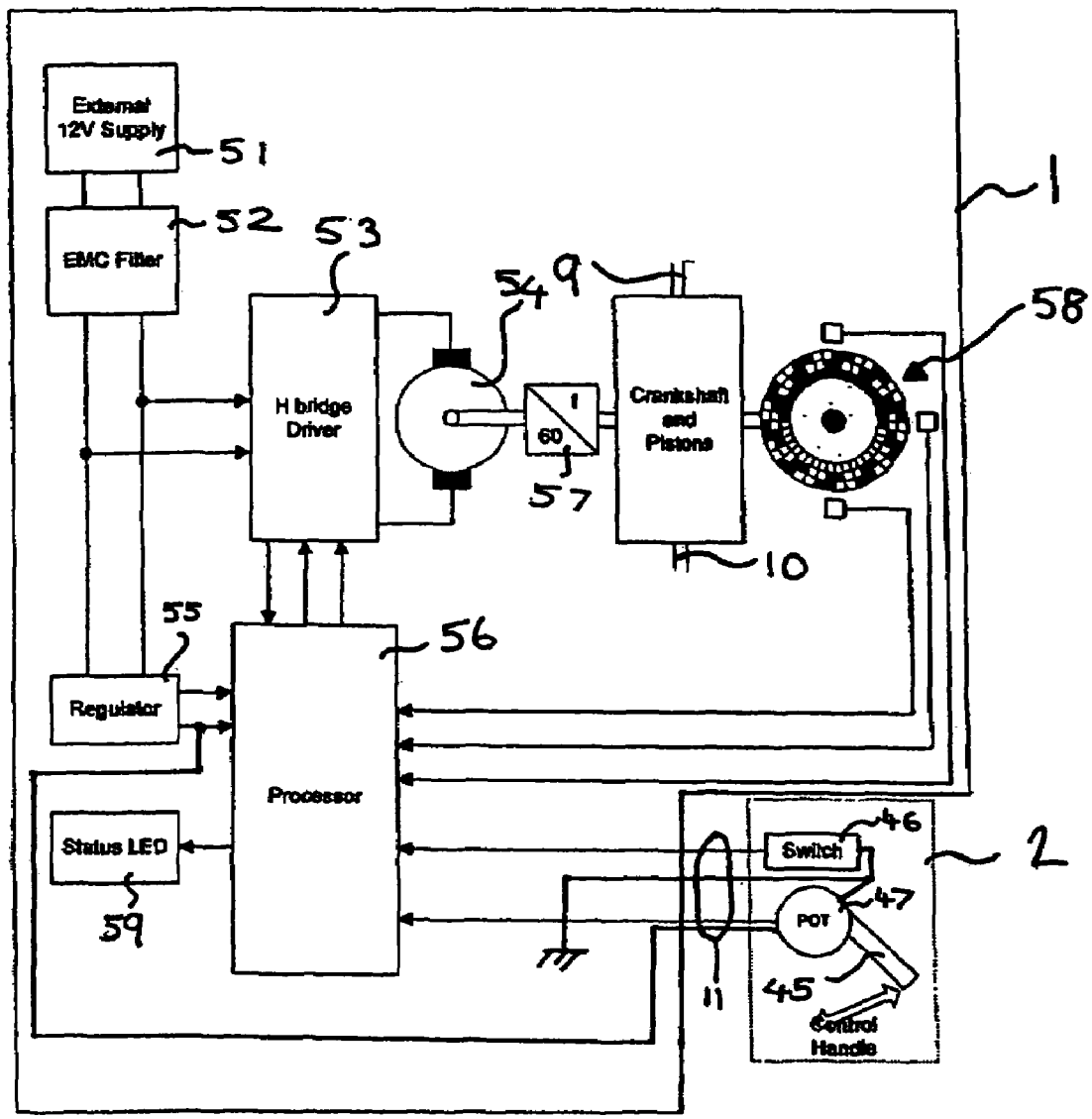
FIG. 5 is a block diagram of the actuating pump and its control system.

Referring to FIG. 5, the system is powered from an external 12V source 51. The power from the external source 51 is filtered by an EMC filter 52 and provided to a H-bridge circuit 53, which provides power to a motor 54, and a regulator 55. The regulated output of the regulator 55 powers the processing circuit 56 which is built around a microcontroller.

The motor 54 drives a crankshaft back and forth over a range of up to 180° via a 60:1 reduction gear 57. A pair of pistons are driven via a 1:1 gear train from the crankshaft. The movement of the pistons pumps air out of and into the master and slave heads 2, 3 via the flexible tubes 9, 10. The angular position of the crankshaft is sensed by a rotary encoder 58.

A status LED 59 is controlled by an output from the control circuit 56 to provide feedback to the user.

The switch 46 is coupled between an interrupt input of the processing circuit 56 and ground. The potentiometer 47 is coupled between the positive voltage output of the regulator 55 and ground, and the wiper of the potentiometer 47 is connected to an analogue-to-digital converter input of the processing circuit 56.

The processing circuit 56 provides motor speed and direction signals to H-bridge circuit 53 to control the movement of the motor 54.

The operation of the system will now be described.

Figure 6:
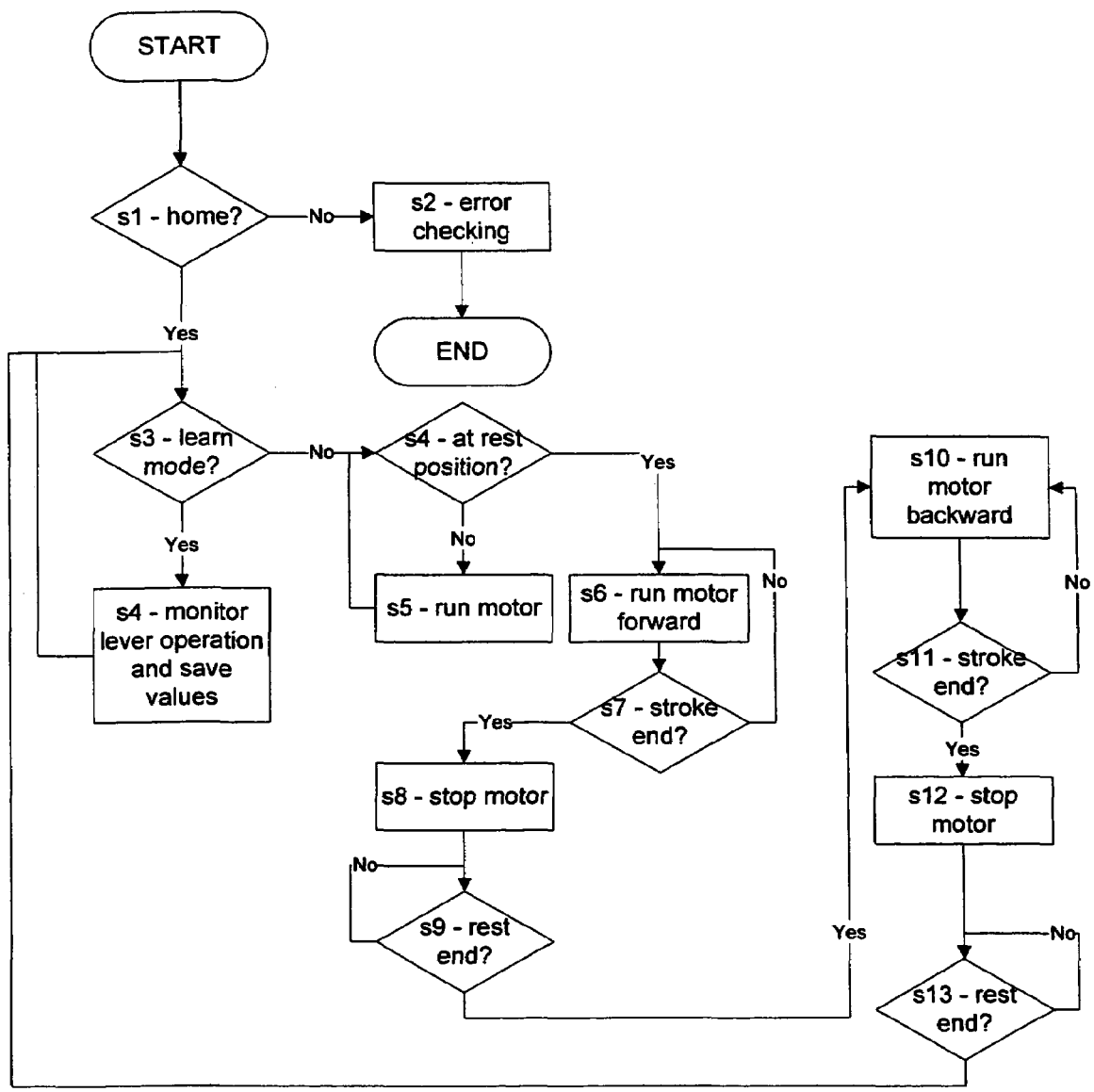
FIG. 6 is a flowchart illustrating the operation of the system in FIG. 1.

Referring to FIG. 6, when the system is turned on, the processing circuit 56 determines whether the crank is in its home position by comparing the output of the rotary encoder 58 with a home reference value, i.e. 0 (step s1). If the crank is not in its home position, the processing circuit performs an error checking routine and signals any errors using the status LED 59 (step s2) and halts the system.

Figure 7:
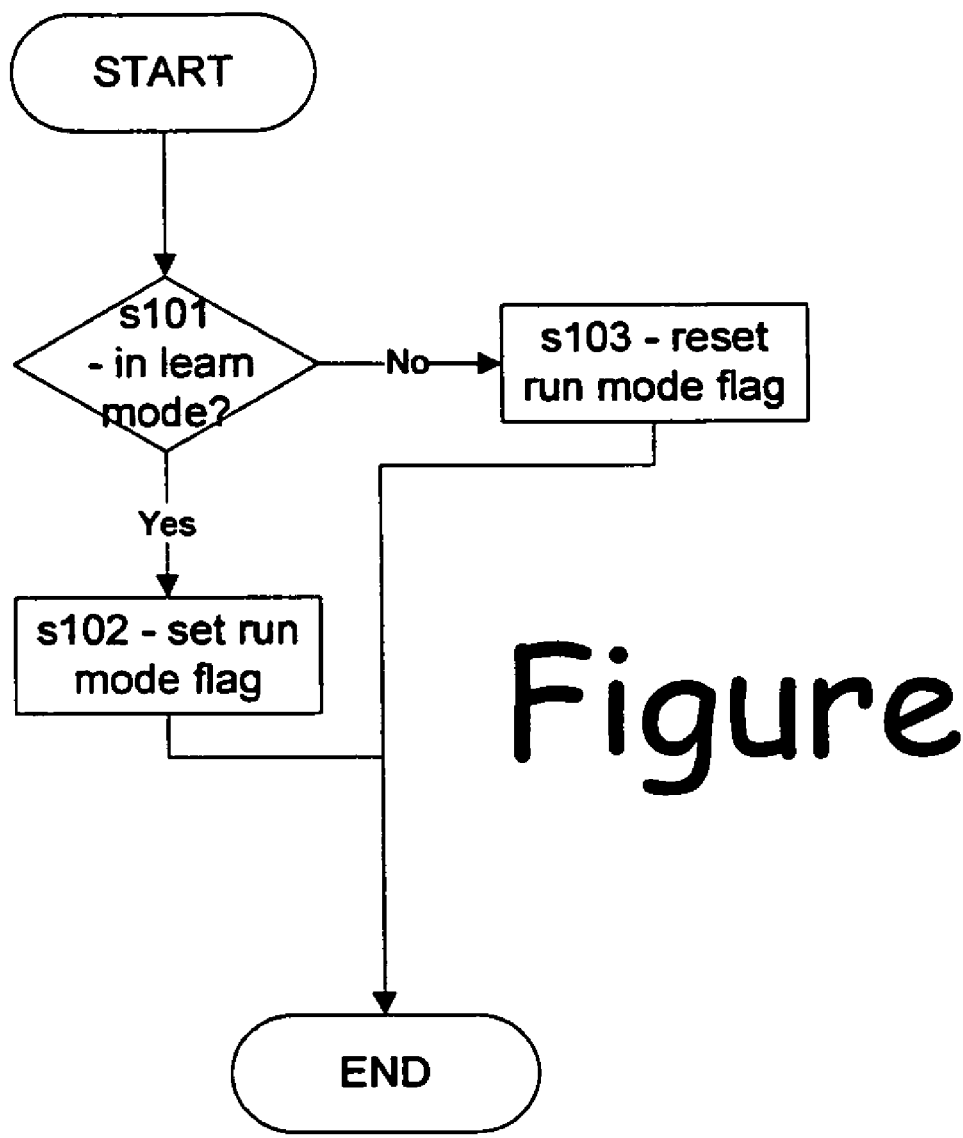
FIG. 7 is a flowchart illustrating mode changing of the system in FIG. 1.

The system enters "learn" mode by default. However, referring to FIG. 7, closing the switch 46 while the system is in "learn" mode switches it to "run" by setting a run mode flag (steps s101 and s102) and closing the switch 46 while the system is in "run" mode will switch it back to "learn" mode by resetting the run mode flag (steps s101 and s103).

In "learn" mode (step s3), the motor 54 is controlled by the processing circuit 56 in a simple servo loop (step s4). As the user presses the lever 45 towards the body 7, to which the master head 2 is mounted, the wiper of the potentiometer 47 moves changing the output voltage of the potentiometer 47. This voltage is digitised and compared with the output of the rotary encoder and any error is used to generate control signal to drive the motor 56 so as to remove the error. Pressing the lever 45 causes the motor 54 to move the pistons in the down stroke directions, causing the diaphragms 25 to rise and apply a sucking force in the breast receiving trumpets 23, and allowing the lever 45 to move towards its rest position causes the motor 54 to move the pistons in the up stroke direction, relieving the sucking force. Thus, the pressure in the trumpet 23 is set by the position of the lever 44 and the user can experiment by pressing and releasing the lever 45 until a comfortable and effective cycle has been discovered.

Figure 8:
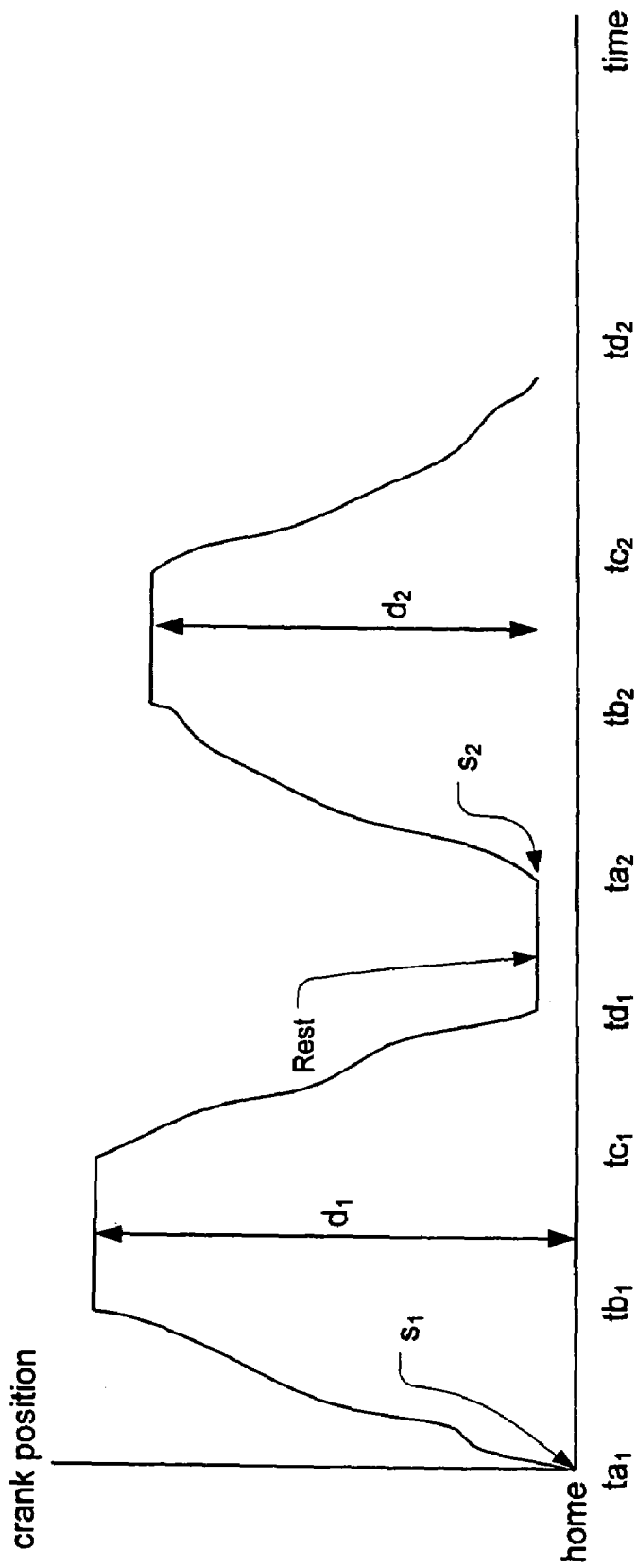
FIG. 8 is a plot illustrating two exemplary pumping cycles during "learn" mode operation of the system in FIG. 1.

Referring to FIG. 8, during operation in the "learn" mode, the processing circuit 56 monitors the times of the start of each suctions stroke (ta), the end of each suction stroke (tb), the start of each relaxation stroke (tc) and the end of each relaxation stroke (td). The processing circuit 56 also monitors the start position (s) and lengths (d) of each suction stroke.

Figure 9:
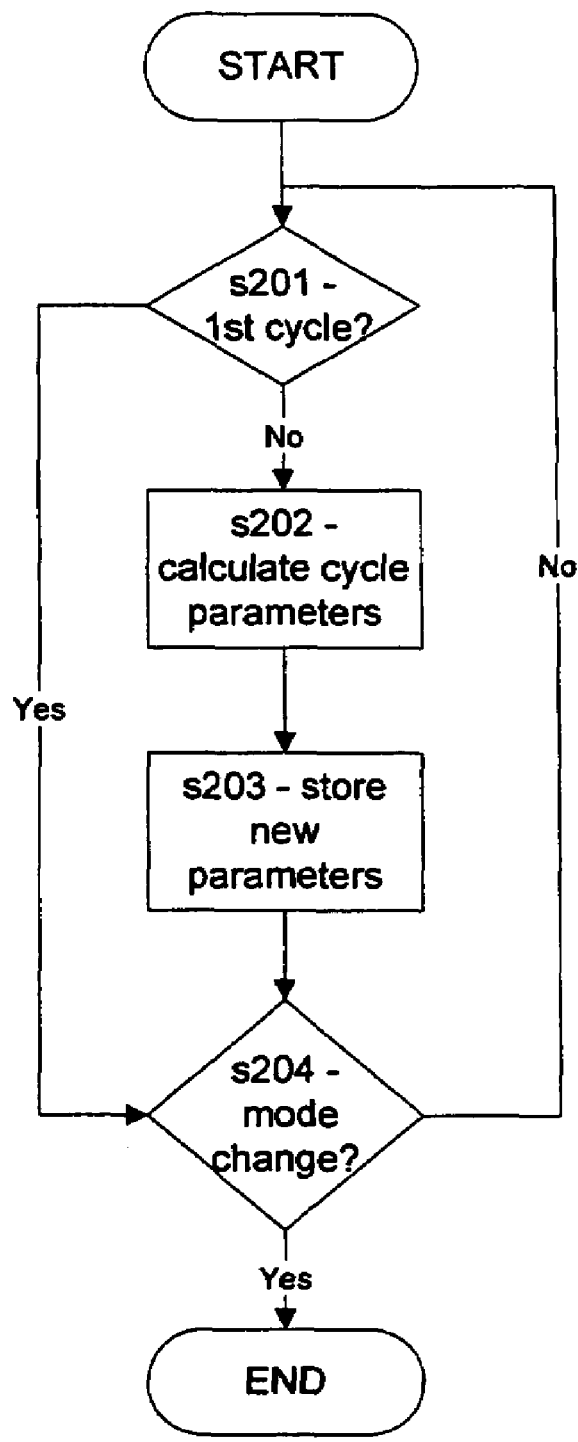
FIG. 9 is a flowchart illustrating part of the "learn" mode operation in detail.

Referring to FIG. 9, at the end of the second and each subsequent relaxation stroke, i.e. at $td_n$, (step s201) the processing circuit 56 calculates the suction stroke velocity (i.e. d/(tb–ta)), the suction hold period, the relaxation stroke velocity (i.e. d/td–tc)) and the rest period of the previous cycle (if any) are calculated from the monitored times for the current and preceding cycles (step s202) and stored (step s203). The state of the run mode flag is then checked (step s204) and if the mode has changed to "run" mode, "learn" mode is left otherwise the process returns to step s101.

When the system is switched to "run" mode by the user closing the switch 44, the processing circuit 56 controls the motor 54 in accordance with the stored velocities and periods and the stored stroke and depth value.

Referring to FIGS. 6 and 10, if the system is determined to be in "run" mode (step s3), the processing circuit 56 determines whether the crankshaft is in the rest position, i.e. the suction stroke start position, (step s4) and, if it is not, outputs a stream of pulses to the H-bridge circuit 53, for setting the speed of the motor 54, and a direction signal so that the pistons move on their up or down stokes at the stored average suction velocity (step s5) until the rest position is reached. When the crankshaft is in the rest position (step s4), the processing circuit 56 beings to output a stream of motor speed control pulses to the H-bridge circuit 53 together with a forward signal for causing the motor 54 to run in a first direction (step s6). These pulses and the forward signal are output until the output of the rotary encoder 58 matches the sum of the rest position and the stored stroke depth value (step s7) at which time the motor is stopped (step s8). When the motor has been stopped, the processing circuit 56 does not output anymore speed control pulses until a period corresponding to the stored suction hold period has expired (step s9). When the suction hold period has expired (step s9), the processing circuit 56 outputs speed control pulses, corresponding to the stored average relaxation stroke velocity, to the H-bridge circuit 53 together with a reverse signal (step s9). These signals cause the motor to be driven in a second, opposite direction, driving the pistons on their up strokes, and are terminated when the rotary encoder 58 indicates that the pump has returned to its rest position (steps s11 and s12). The processing circuit 56 does not then output any further motor control signals and when the stored average rest period has expired (step s13), it returns to step s3.

The system can be operated by a user in "learn" mode without switching to "run" mode. Thus, the system also provides a power-assisted breast pump which gives the user continuous control over the pumping cycle as with manual breast pumps but without the physical effort required by a manual breast pump.

It will be appreciated that the present invention can be implemented in other ways. For example, the "run" mode cycles could follow the "learn" mode cycle with greater fidelity. This could be achieved by recording the position of the crankshaft at a plurality of instants during each stroke in "learn" mode. The "run" mode cycle could be established by taking averages of cycle parameters obtained from a plurality of learn mode cycles. For convenience, the user input means mimics the actuator of a manual breast pump. This arrangement could be replaced by a foot switch and pedal rather like that of a sewing machine or a separate handheld control unit. The user inputs may be communicated to the processing circuit wirelessly, e.g. using IR.

An alternative to the suction start parameter and stroke length parameter combination would be a rest position parameter and suction hold position parameter.

It will be appreciated that many modifications may be made to the embodiment described above without departing from the spirit and scope of the claims appended hereto.

What is claimed is:

1. A powered breast pump system, comprising:
   a motorised breast pump;
   a user input mechanism; and
   a controller configured to control the pumping operation of motorised breast pump such that the suction produced by the pump follows a suction level control signal, produced by operation of the user input mechanism that allows independent adjustment of suction force and suction cycle during pumping.

2. A system according to claim 1, wherein the controller is configured to operate the motorised breast pump in a learn mode, in which said suction level control signal is followed, and a run mode, in which the controller controls the pumping operation of the motorised breast pump so as to mimic previous learn mode operation.

3. A system according to claim 2, wherein the controller is configured to store parameters defining a pump operation cycle during learn mode operation.

4. A system according to claim 3, wherein said parameters are selected from a list comprising: suction stroke average velocity, relaxation stroke average velocity, suction hold duration, rest hold duration, suction stroke length, and suction stroke start position.

5. A system according to claim 1, wherein the motorised breast pump comprises a motorised pump unit, a handheld unit for receiving a user's breast and capturing expressed milk and tubing connecting the pump unit to the handheld unit and containing a working fluid which is pumped back and forth by the motorised pump unit for varying the pressure within a milk receiving chamber in the handheld unit.

6. A system according to claim 5, wherein the handheld unit includes a flexible diaphragm separating the working fluid from the milk receiving chamber.

7. A system according to claim 5, wherein the motorised pump unit comprises two pumps connected to respective handheld units by respective tubes and driven in phase by a shared motor.

8. A system according to claim 5, wherein the or each handheld unit comprises a removable head comprising the diaphragm and a cap connected to the associated tube.

9. A system according to claim 8, wherein the or each diaphragm and the associated cap or caps are separable.

10. A system according to claim 8, including a manual head comprising a diaphragm and operating means for manually operating the diaphragm for varying the pressure in the milk receiving chamber, wherein the manual head is interchangeable with said removable head.

11. A system according to claim 1, including a manual head comprising operating means for manually varying the pressure in a milk receiving chamber, wherein the manual head is interchangeable with a motor driven head.

12. A system according to claim 11, wherein the user input means are mechanism is configured such that the user operations for producing said suction level control signal resemble the user operation of the operating means for manually pumping.

13. A system according to claim 12, wherein the operating means comprises a lever.

14. A powered breast pump system, comprising:
   a motorised breast pump;
   user input means; and
   a controller configured to operate the motorised breast pump in a learn mode and a run mode, wherein, in the learn mode, the controller controls the pumping operation of motorised breast pump such that the suction produced by the pump follows a suction level control signal, produced by operation of the user input means during pumping, and, in the run mode, the controller controls the pumping operation of the motorised breast pump so as to mimic previous learn mode operation.

15. A system according to claim 14, wherein the motorised breast pump comprises a motorised pump unit, a handheld unit for receiving a user's breast and capturing expressed milk and tubing connecting the pump unit to the handheld unit and containing a working fluid which is pumped back and forth by the motorised pump unit for varying the pressure within a milk receiving chamber in the handheld unit.

16. A system according to claim 15, wherein the handheld unit includes a flexible diaphragm separating the working fluid from the milk receiving chamber.

17. A system according to claim 15, wherein the motorised pump unit comprises two pumps connected to respective handheld units by respective tubes and driven in phase by a shared motor.

18. A system according to claim 15, wherein the or each handheld unit comprises a removable head comprising the diaphragm and a cap connected to the associated tube.

19. A system according to claim 18, wherein the or each diaphragm and the associated cap or caps are separable.

20. A system according to claim 18, including a manual head comprising a diaphragm and operating means for manually operating the diaphragm for varying the pressure in the milk receiving chamber, wherein the manual head is interchangeable with said removable head.

21. A system according to claim 14, including a manual head comprising operating means for manually varying the pressure in a milk receiving chamber, wherein the manual head is interchangeable with a motor driven head.

22. A system according to claim 21, wherein the user input means are configured such that the user operations for producing said suction level control signal resemble the user operation of the operating means for manually pumping.

23. A system according to claim 22, wherein the operating means comprises a lever.

* * * * *